United States Patent
Forsell

(10) Patent No.: US 8,463,394 B2
(45) Date of Patent: Jun. 11, 2013

(54) METHOD AND APPARATUS FOR SUPPLYING ENERGY TO A MEDICAL DEVICE

(75) Inventor: Peter Forsell, Zug (CH)

(73) Assignee: Teslux Holding SA, Luxembourg (LU)

( * ) Notice: Subject to any disclaimer, the term of this patent is extended or adjusted under 35 U.S.C. 154(b) by 0 days.

(21) Appl. No.: 12/682,831

(22) PCT Filed: Oct. 10, 2008

(86) PCT No.: PCT/SE2008/000563
§ 371 (c)(1),
(2), (4) Date: Apr. 13, 2010

(87) PCT Pub. No.: WO2009/051538
PCT Pub. Date: Apr. 23, 2009

(65) Prior Publication Data
US 2010/0222848 A1      Sep. 2, 2010

Related U.S. Application Data

(60) Provisional application No. 60/960,861, filed on Oct. 17, 2007, provisional application No. 60/960,832, filed on Oct. 16, 2007, provisional application No. 60/996,601, filed on Nov. 27, 2007.

(51) Int. Cl.
*A61N 1/00*     (2006.01)

(52) U.S. Cl.
USPC .......................................................... 607/61

(58) Field of Classification Search
USPC .......................................................... 607/61
See application file for complete search history.

(56) References Cited

U.S. PATENT DOCUMENTS

| | | | |
|---|---|---|---|
| 4,679,560 A | 7/1987 | Galbraith | |
| 5,591,212 A | 1/1997 | Keimel | |
| 5,702,431 A | 12/1997 | Wang et al. | |
| 5,713,939 A * | 2/1998 | Nedungadi et al. | 607/33 |

(Continued)

FOREIGN PATENT DOCUMENTS

| EP | 1 513 241 | 3/2005 |
|---|---|---|
| EP | 1 609 501 | 12/2005 |

(Continued)

OTHER PUBLICATIONS

International Search Report for PCT/SE2008/000563, mailed Feb. 5, 2009.

(Continued)

*Primary Examiner* — Christopher D Koharski
*Assistant Examiner* — Philip Edwards
(74) *Attorney, Agent, or Firm* — Nixon & Vanderhye P.C.

(57) ABSTRACT

In a method and apparatus for supplying wireless energy to a medical device (100) implanted in a patient, wireless energy is transmitted from an external energy source (104) located outside a patient and is received by an internal energy receiver (102) located inside the patient, for directly or indirectly supplying received energy to the medical device. An energy balance is determined between the energy sent by the external energy source and energy received by the internal energy receiver, and the transmission of wireless energy is then controlled based on the determined energy balance. The energy balance thus provides an accurate indication of the correct amount of energy needed, which is sufficient to operate the medical device properly, but without causing undue temperature rise.

21 Claims, 3 Drawing Sheets

U.S. PATENT DOCUMENTS

| | | | |
|---|---|---|---|
| 5,735,887 A * | 4/1998 | Barreras et al. | 607/60 |
| 5,876,425 A * | 3/1999 | Gord et al. | 607/56 |
| 6,442,434 B1 | 8/2002 | Zarinetchi et al. | |
| 6,745,077 B1 * | 6/2004 | Griffith et al. | 607/61 |
| 2004/0039423 A1 * | 2/2004 | Dolgin | 607/27 |
| 2005/0075697 A1 * | 4/2005 | Olson et al. | 607/61 |
| 2006/0030887 A1 | 2/2006 | Letort et al. | |
| 2007/0156204 A1 | 7/2007 | Denker et al. | |
| 2010/0211133 A1 | 8/2010 | Forsell | |
| 2010/0211134 A1 | 8/2010 | Forsell | |
| 2010/0217352 A1 | 8/2010 | Forsell | |
| 2010/0217353 A1 | 8/2010 | Forsell | |
| 2010/0222849 A1 | 9/2010 | Forsell | |
| 2010/0234922 A1 | 9/2010 | Forsell | |
| 2011/0193688 A1 | 8/2011 | Forsell | |
| 2011/0196452 A1 | 8/2011 | Forsell | |
| 2011/0278948 A1 | 11/2011 | Forsell | |
| 2011/0301668 A1 | 12/2011 | Forsell | |
| 2012/0112556 A1 | 5/2012 | Forsell | |
| 2012/0119700 A1 | 5/2012 | Forsell | |

FOREIGN PATENT DOCUMENTS

| | | |
|---|---|---|
| WO | WO 01/58389 | 8/2001 |
| WO | WO 03/002192 | 1/2003 |
| WO | WO 2004/018037 | 3/2004 |
| WO | WO 2005/084730 | 9/2005 |

OTHER PUBLICATIONS

Written Opinion of the International Searching Authority for PCT/SE2008/000563, mailed Feb. 5, 2009.
U.S. Appl. No. 13/384,387 (Forsell) filed Jan. 17, 2012.
U.S. Appl. No. 13/384,039 (Forsell) filed Jan. 13, 2012.
U.S. Appl. No. 13/130,648 (Forsell) filed Aug. 3, 2011.
U.S. Appl. No. 13/130,634 (Forsell) filed Aug. 3, 2011.
U.S. Appl. No. 13/123,638 (Forsell) filed Apr. 11, 2011.
U.S. Appl. No. 13/123,168 (Forsell) filed Apr. 7, 2011.
U.S. Appl. No. 12/738,182 (Forsell) filed Apr. 15, 2010.
U.S. Appl. No. 12/682,835 (Forsell) filed Apr. 13, 2010.
U.S. Appl. No. 12/682,477 (Forsell) filed Apr. 9, 2010.
U.S. Appl. No. 12/682,404 (Forsell) filed Apr. 9, 2010.
U.S. Appl. No. 12/682,336 (Forsell) filed Apr. 9, 2010.
U.S. Appl. No. 12/682,327 (Forsell) filed Apr. 9, 2010.

* cited by examiner

METHOD AND APPARATUS FOR SUPPLYING ENERGY TO A MEDICAL DEVICE This application is the U.S. national phase of International Application No. PCT/SE2008/000563 filed 10 Oct. 2008, which designated the U.S. and claims the benefit of U.S. Provisional Appln. No. 60/960,832 filed 16 Oct. 2007; U.S. Provisional Appln. No. 60/960,861 filed 17 Oct. 2007; and U.S. Provisional Appln. No. 60/996,601 filed 27 Nov. 2007, the entire contents of each of which are hereby incorporated by reference.

TECHNICAL FIELD

The present invention relates generally to a method and apparatus for supplying wireless energy to a medical device implanted in a patient. In particular, the invention is concerned with controlling the amount of energy transferred from an energy source outside the patient to an energy receiver inside the patient.

BACKGROUND

Medical devices, designed to be implanted in a patient's body, are typically operated by means of electrical power. Such medical devices include electrical and mechanical stimulators, motors, pumps, etc, which are designed to support or stimulate various body functions. Electrical power can be supplied to such an implanted medical device from a likewise implanted battery or from an external energy source that can supply any needed amount of electrical power intermittently or continuously without requiring repeated surgical operations.

An external energy source can transfer wireless energy to an implanted internal energy receiver located inside the patient and connected to the medical device for supplying received energy thereto. So-called TET (Transcutaneous Energy Transfer) devices are known that can transfer wireless energy in this manner. Thereby, no leads or the like penetrating the skin need to be used for connecting the medical device to an external energy source, such as a battery.

A TET device typically comprises an external energy source including a primary coil adapted to inductively transfer any amount of wireless energy, by inducing voltage in a secondary coil of an internal energy receiver which is implanted preferably just beneath the skin of a patient. The highest transfer efficiency is obtained when the primary coil is positioned close to the skin adjacent to and in alignment with the secondary coil, i.e. when a symmetry axis of the primary coil is parallel to that of the secondary coil.

Typically, the amount of energy required to operate an implanted medical device may vary over time depending on the operational characteristics of the device. For example, the device may be designed to switch on and off at certain intervals, or otherwise change its behavior, in order to provide a suitable electrical or mechanical stimulation, or the like. Such operational variations will naturally result in corresponding variations with respect to the amount of required energy.

Furthermore, the position of the external energy source relative to the implanted internal energy receiver is a factor that affects the efficiency of the energy transfer, which highly depends on the distance and relative angle between the source and the receiver. For example, when primary and secondary coils are used, changes in coil spacing result in a corresponding variation of the induced voltage. During operation of the medical device, the patient's movements will typically change the relative spacing of the external source and the internal receiver arbitrarily such that the transfer efficiency greatly varies.

If the transfer efficiency becomes low, the amount of energy supplied to the medical device may be insufficient for operating the device properly, so that its action must be momentarily stopped, naturally disturbing the intended medical effect of the device.

On the other hand, the energy supplied to the medical device may also increase drastically, if the relative positions of the external source and the internal receiver change in a way that unintentionally increases the transfer efficiency. This situation can cause severe problems since the implant cannot "consume" the suddenly very high amount of supplied energy. Unused excessive energy must be absorbed in some way, resulting in the generation of heat, which is highly undesirable. Hence, if excessive energy is transferred from the external energy source to the internal energy receiver, the temperature of the implant will increase, which may damage the surrounding tissue or otherwise have a negative effect on the body functions. It is generally considered that the temperature in the body should not increase more than three degrees to avoid such problems.

It is thus highly desirable to always supply the right amount of energy to an implanted medical device, in order to ensure proper operation and/or to avoid increased temperature. Various methods are known for controlling the amount of transferred energy in response to different conditions in the receiving implant. However, the presently available solutions for controlling the wireless transfer of energy to implanted medical devices are lacking in precision in this respect.

For example, U.S. Pat. No. 5,995,874 discloses a TET system in which the amount of transmitted energy from a primary coil is controlled in response to an indication of measured characteristics of a secondary coil, such as load current and voltage. The transmitted energy can be controlled by varying the current and voltage in the primary coil, transmission frequency or coil dimensions. In particular, a change is effected in the saturation point of the magnetic field between the coils, in order to adjust the power transfer efficiency. However, it is not likely that this solution will work well in practice, since a saturation point in the human tissue would not occur, given the magnetic field levels that are possible to use. Moreover, if the energy transmission must be increased considerably, e.g. to compensate for losses due to variations in alignment and/or spacing between the coils, the relatively high radiation generated may be damaging or unhealthy or unpleasant to the patient, as is well known.

An effective solution is thus needed for accurately controlling the amount of transferred energy to an implanted medical device to ensure proper operation thereof. Moreover, excessive energy transfer resulting in raised temperature at the medical device, and/or power surges should be avoided, in order to avoid tissue damages and other unhealthy or unpleasant consequences for the patient.

SUMMARY OF THE INVENTION

A method is thus provided for controlling transmission of wireless energy supplied to an electrically operable medical device implanted in a patient. The wireless energy is transmitted from an external energy source located outside the patient and is received by an internal energy receiver located inside the patient, the internal energy receiver being connected to the medical device for directly or indirectly supplying received energy thereto. An energy balance is determined between the energy sent by the external energy source and the energy received by the internal energy receiver. The transmission of wireless energy from the external energy source is then controlled based on the determined energy balance.

An apparatus is also provided for controlling transmission of wireless energy supplied to an electrically operable medical device implanted in a patient. The apparatus is adapted to transmit the wireless energy from an external energy source located outside the patient which is received by an internal energy receiver located inside the patient, the internal energy receiver being connected to the medical device for directly or indirectly supplying received energy thereto. The apparatus is further adapted to determine an energy balance between the energy sent by the external energy source and the energy received by the internal energy receiver, and to control the transmission of wireless energy from the external energy source, based on the determined energy balance.

The method and apparatus may be implemented according to different embodiments and features as follows:

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed (e.g. by the consuming part 200*a* of FIG. 2) to operate the medical device. In that case, the energy may be consumed after being stabilized in at least one energy stabilizing unit of the medical device.

In another alternative, substantially all energy used for the medical device is stored in the at least one energy storage device. In yet another alternative, the energy used for the medical device is partly consumed to operate the medical device and partly stored in the at least one energy storage device.

The energy received by the internal energy receiver may be stabilized by a capacitor, before the energy is supplied directly or indirectly to the medical device.

The difference between the total amount of energy received by the internal energy receiver and the total amount of consumed and/or stored energy may be directly or indirectly measured over time, and the energy balance can then be determined based on a detected change in the total amount difference.

The energy received by the internal energy receiver may further be accumulated and stabilized in an energy stabilizing unit, before the energy is supplied to the medical device. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment is corresponding to the rate of the change at the first given moment, wherein the rate of change includes the direction and speed of the change. The derivative may further be determined based on a detected rate of change of the electrical parameter.

The energy received by the internal energy receiver may be supplied to the medical device with at least one constant voltage, wherein the constant voltage is created by a constant voltage circuitry. In that case, the energy may be supplied with at least two different voltages, including the at least one constant voltage.

The energy received by the internal energy receiver may also be supplied to the medical device with at least one constant current, wherein the constant current is created by a constant current circuitry. In that case, the energy may be supplied with at least two different currents including the at least one constant current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device in the medical device may include at least one of a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device with at least one constant voltage, as maintained by a constant voltage circuitry. In that case, the medical device and energy storage device may be supplied with two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device with at least one constant current, as maintained by a constant current circuitry. In that case, the medical device and energy storage device may be supplied with two different currents wherein at least one current is constant, maintained by the constant current circuitry.

The wireless energy may be initially transmitted according to a predetermined energy consumption plus storage rate. In that case, the transmission of wireless energy may be turned off when a predetermined total amount of energy has been transmitted. The energy received by the internal energy receiver may then also be accumulated and stabilized in an energy stabilizing unit before being consumed to operate the medical device and/or stored in the energy storage device until a predetermined total amount of energy has been consumed and/or stored.

Further, the wireless energy may be first transmitted with the predetermined energy rate, and then transmitted based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance, can be determined by detecting the direction and rate of change in the current amount of accumulated energy in the energy stabilizing unit.

The transmission of wireless energy may be controlled such that an energy reception rate in the internal energy receiver corresponds to the energy consumption and/or storage rate. In that case, the transmission of wireless energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit. Suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transmitted with a transmission rate which is determined based on the parameters. Further, the transmission of wireless energy may be controlled such that the total amount of transmitted energy is based on said parameters.

The energy received by the internal energy receiver may be first accumulated and stabilized in an energy stabilizing unit, and then consumed until a predetermined total amount of energy has been consumed. The transmission of wireless energy may further be controlled such that an energy reception rate at the internal energy receiver corresponds to a predetermined energy consumption rate.

Further, electrical and/or physical parameters of the medical device and/or physical parameters of the patient may be determined, in order to determine the total amount of transmitted energy based on the parameters. In that case, the energy received by the internal energy receiver may be first accumulated and stabilized in an energy stabilizing unit, and then consumed until a predetermined total amount of energy has been consumed.

The energy is stored in the energy storage device according to a predetermined storing rate. The transmission of wireless energy may then be turned off when a predetermined total amount of energy has been stored. The transmission of, wireless energy can be further controlled such that an energy reception rate at the internal energy receiver corresponds to the predetermined storing rate.

The energy storage device of the medical device may comprise a first storage device and a second storage device, wherein the energy received by the internal energy receiver is first stored in the first storage device, and the energy is then supplied from the first storage device to the second storage device at a later stage.

When using the first and second storage devices in the energy storage device, the energy balance may be determined in different ways. Firstly, the energy balance may be determined by detecting the current amount of energy stored in the first storage device, and the transmission of wireless energy may then be controlled such that a storing rate in the second storage device corresponds to an energy reception rate in the internal energy receiver. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device with a constant current, as maintained by a constant current circuitry, until a measured voltage over the second storage device reaches a predetermined maximum voltage, and thereafter supplied from the first storage device to the second storage energy storage device with a constant voltage, as maintained by a constant voltage circuitry. In that case, the transmission of wireless energy may be turned off when a predetermined minimum rate of transmitted energy has been reached.

The transmission of energy may further be controlled such that the amount of energy received by the internal energy receiver corresponds to the amount of energy stored in the second storage device. In that case, the transmission of energy may be controlled such that an energy reception rate at the internal energy receiver corresponds to an energy storing rate in the second storage device. The transmission of energy may also be controlled such that a total amount of received energy at the internal energy receiver corresponds to a total amount of stored energy in the second storage device.

In the case when the transmission of wireless energy is turned off when a predetermined total amount of energy has been stored, electrical and/or physical parameters of the medical device and/or physical parameters of the patient may be determined during a first energy storing procedure, and the predetermined total amount of energy may be stored in a subsequent energy storing procedure based on the parameters.

When electrical and/or physical parameters of the medical device and/or physical parameters of the patient are determined, the energy may be stored in the energy storage device with a storing rate which is determined based on the parameters. In that case, a total amount of energy may be stored in the energy storage device, the total amount of energy being determined based on the parameters. The transmission of wireless energy may then be automatically turned off when the total amount of energy has been stored. The transmission of wireless energy may further be controlled such that an energy reception rate at the internal energy receiver corresponds to the storing rate.

When electrical and/or physical parameters of the medical device and/or physical parameters of the patient are determined, a total amount of energy may be stored in the energy storage device, the total amount of energy being determined based on said parameters. The transmission of energy may then be controlled such that the total amount of received energy at the internal energy receiver corresponds to the total amount of stored energy. Further, the transmission of wireless energy may be automatically turned off when the total amount of energy has been stored.

When the energy used for the medical device is partly consumed and partly stored, the transmission of wireless energy may be controlled based on a predetermined energy consumption rate and a predetermined energy storing rate. In that case, the transmission of energy may be turned off when a predetermined total amount of energy has been received for consumption and storage. The transmission of energy may also be turned off when a predetermined total amount of energy has been received for consumption and storage.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When electrical and/or physical parameters of the medical device and/or physical parameters of the patient are determined, the energy may be supplied from the energy storage device to the medical device for consumption with a supply rate which is determined based on said parameters. In that case, the total amount of energy supplied from the energy storage device to the medical device for consumption, may be based on said parameters.

When electrical and/or physical parameters of the medical device and/or physical parameters of the patient are determined, a total amount of energy may be supplied to the medical device for consumption from the energy storage device, where the total amount of supplied energy is determined based on the parameters.

When the energy received by the internal energy receiver is accumulated and stabilized in an energy stabilizing unit, the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

When using the first and second storage devices in the energy storage device, the second storage device may directly or indirectly supply energy to the medical device, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or current related to the energy, balance.

The first storage device may include at least one of: a capacitor and a semiconductor, and the second storage device includes at least one of: a rechargeable battery, an accumulator and a capacitor.

As mentioned above, the wireless energy may be transmitted inductively from a primary coil in the external energy source to a secondary coil in the internal energy receiver. However, the wireless energy may also be transmitted non-inductively. For example, the wireless energy may be transmitted by means of sound or pressure variations, radio or light. The wireless energy may also be transmitted in pulses or waves and/or by means of an electric field.

When the wireless energy is transmitted from the external energy source to the internal energy receiver in pulses, the transmission of wireless energy may be controlled by adjusting the width of the pulses.

When the difference between the total amount of energy received by the internal energy receiver and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using the first and second storage devices in the energy storage device, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater life-time in terms of charging occasions. The first storage device may comprise at least one capacitor. Normally, only the first storage may be charged and more often than needed for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When electrical parameters of the medical device are determined, the charging of the second storage device may be controlled based on the parameters. A constant current or stabilizing voltage circuitry may be used for storing energy in the second storage device.

A method is thus provided for controlling transmission of wireless energy supplied to an electrically operable medical device implanted in a mammal patient. The wireless energy is transmitted by means of a primary coil in an external energy source located outside the patient and received inductively by means of a secondary coil in an internal energy receiver located inside the patient. The internal energy receiver is connected to the medical device for directly or indirectly supplying received energy thereto. Feedback control information is transferred from the secondary coil to the primary coil by switching the secondary coil on and off to induce a detectable impedance load variation in the primary coil encoding the feedback control information. The feedback control information relates to the energy received in the medical device and is used for controlling the transmission of wireless energy from the external energy source.

An apparatus is also provided for controlling transmission of wireless energy supplied to an electrically operable medical device implanted in a mammal patient. The apparatus comprises an external energy source adapted to transmit the wireless energy by means of a primary coil when located outside the patient, and an internal energy receiver adapted to receive the transmitted wireless energy inductively by means of a secondary coil when located inside the patient, and to directly or indirectly supply received energy to the medical device. The internal energy receiver is further adapted to transfer feedback control information from the secondary coil to the primary coil in accordance with the above method.

The method and apparatus may be implemented according to different embodiments and features as follows:

In one embodiment, an internal control unit controls the on and off switching of the secondary coil, wherein the feedback control information may include at least one predetermined parameter relating to the received energy. The predetermined parameter may also be variable. The feedback control information may also relate to the received energy and require artificial intelligence to be generated. An implantable switch may be used to execute the on and off switching of the secondary coil as controlled by the internal control unit. The switch may be an electronic switch such as a transistor. Further, the internal control unit may comprise a memory for storing the transferred feedback control information.

In another embodiment, an internal control unit determines an energy balance between the energy received by the internal energy receiver and the energy used for the medical device, where the feedback control information relates to the determined energy balance. An external control unit then controls the transmission of wireless energy from the external energy source based on the determined energy balance and using the feedback control information.

Further embodiments comprises

An apparatus, wherein the feedback information is related to the amount of energy being received in the internal energy receiver.

An apparatus, wherein the external energy source further comprises an electronic circuit for comparing the feedback information with the amount of energy transmitted by the external energy source.

A apparatus, wherein the electronic circuit comprises an analyzer adapted to analyze the amount of energy being transmitted and adapted to receive the feedback information related to the amount of energy received in the receiver, and further adapted to determine the special energy balance by comparing the amount of transmitted energy and the feedback information related to the amount of received information.

An apparatus, wherein the external energy source is adapted to use said feedback information to adjust the level of said transmitted energy.

A apparatus, wherein the external energy source is adapted to transfer data related to the amount of transmitted energy to the receiver, and wherein the feedback information is related to the amount of energy received in the receiver the receiver compared to the amount of said transmitted energy.

An apparatus, wherein external energy source is adapted to use said feedback information to adjust the level of said transmitted energy.

An apparatus, wherein the feedback information is related to a coupling factor between the primary coil and the secondary coil.

An apparatus, wherein the external energy source is adapted to increase the amount of transferred energy to the internal energy receiver until a predetermined response of said coupling factor is detected.

An apparatus, wherein the external energy source further comprises an indicator adapted to indicate a level of the coupling factor.

An apparatus, wherein the external energy source further comprises an indicator adapted to indicate an optimal placement of said secondary coil in relation to said primary coil to optimize said coupling factor.

An apparatus for controlling transmission of wireless energy supplied to an electrically operable medical device (100) when implanted in a mammal patient, the apparatus comprising:

An external energy source (104) adapted to transmit said wireless energy by means of a primary coil when located outside the patient, an internal energy receiver (102) adapted to receive the transmitted wireless energy inductively by means of a secondary coil when located inside the patient, and to directly or indirectly supply received energy to the medical device, wherein the internal energy source is adapted to transfer feedback control information (S) from the secondary coil to the primary coil by switching the secondary coil on and off to induce a detectable impedance load variation in the primary coil encoding the feedback control information, where said feedback control information reflects a required amount of energy for operating the medical device and is used for controlling the transmission of wireless energy from the external energy source.

An apparatus, further comprising an internal control unit (108) adapted to control said on and off switching of the secondary coil, wherein the feedback control information includes at least one predetermined parameter relating to the received energy.

An apparatus, wherein said predetermined parameter is variable.

An apparatus, further comprising an internal control unit (108) adapted to control said on and off switching of the secondary coil, wherein the feedback control information is intelligent and variable relating relates to the received energy and requires artificial intelligence to be generated.

An apparatus, further comprising an implantable switch adapted to execute said on and off switching of the secondary coil as controlled by the internal control unit.

An apparatus, wherein the switch is an electronic switch such as a transistor.

An apparatus, wherein the internal control unit comprises a memory for storing the transferred feedback control information.

An apparatus, further comprising an internal control unit (108) adapted to determine an energy balance between the energy received by the internal energy receiver and the energy used for the medical device, said feedback control information relating to the determined energy balance, and an external control unit (106) adapted to control the transmission of wireless energy from the external energy source based on the determined energy balance and using said feedback control information.

An apparatus, further comprising an external control unit (106) adapted to determine an energy balance between the energy received by the internal energy receiver and the energy used for the medical device based on said feedback control information comprising measurements relating to characteristics of the medical device, and to control the transmission of wireless energy from the external energy source based on the determined energy balance and using said feedback control information.

A method, wherein the feedback information is related to the amount of energy being received in the internal energy receiver.

A method, wherein an electronic circuit in the external energy source compares the feedback information with the amount of energy transmitted by the external energy source.

A method, wherein an analyzer in the electronic circuit analyzes the amount of energy being transmitted and receives the feedback information related to the amount of energy received in the receiver, and further determines the special energy balance by comparing the amount of transmitted energy and the feedback information related to the amount of received information.

A method, wherein the external energy source uses said feedback information to adjust the level of said transmitted energy.

A method, wherein the external energy source transfers data related to the amount of transmitted energy to the receiver, and wherein the feedback information is related to the amount of energy received in the receiver the receiver compared to the amount of said transmitted energy.

A method, wherein external energy source uses said feedback information to adjust the level of said transmitted energy.

A method, wherein the feedback information is related to a coupling factor between the primary coil and the secondary coil.

A method, wherein the external energy source increases the amount of transferred energy to the internal energy receiver until a predetermined response of said coupling factor is detected.

A method, wherein an indicator in the external energy source indicates a level of the coupling factor.

A method, wherein an indicator in the external energy source indicates an optimal placement of said secondary coil in relation to said primary coil to optimize said coupling factor.

A method of controlling transmission of wireless energy supplied to an electrically operable medical device (100) implanted in a mammal patient, said wireless energy being transmitted by means of a primary coil in an external energy source (104) located outside the patient and received inductively by means of a secondary coil in an internal energy receiver (102) located inside the patient, the internal energy receiver being connected to the medical device for directly or indirectly supplying received energy thereto, wherein feedback control information (S) is transferred from the secondary coil to the primary coil by switching the secondary coil on and off to induce a detectable impedance load variation in the primary coil encoding the feedback control information, where the feedback control information reflects the amount of energy received in the medical device and is used for controlling the transmission of wireless energy from the external energy source.

A method, wherein said on and off switching of the secondary coil is controlled by an internal control unit (108), and the feedback control information includes at least one predetermined parameter relating to the received energy.

A method, wherein said predetermined parameter is variable.

A method, wherein said on and off switching of the secondary coil is controlled by an internal control unit (108), and the feedback control information relates to the received energy and requires artificial intelligence to be generated.

A method, wherein said on and off switching of the secondary coil is executed by means of an implantable switch as controlled by the internal control unit.

A method, wherein the switch is an electronic switch such as a transistor.

A method, wherein the transferred feedback control information is stored in a memory of the internal control unit.

A method, wherein an energy balance between the energy received by the internal energy receiver and the energy used for the medical device is determined, said feedback control information relating to the determined energy balance, and the transmission of wireless energy from the external energy source is controlled based on the determined energy balance and using said feedback control information.

A System to Control the Wireless Energy Supply Based on the Feed Back System

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Thus is provided a method of transmitting wireless energy from an external energy transmitting device placed externally to a human body to an internal energy receiver placed internally in the human body, the method comprising:

applying to the external transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Also is provided an apparatus adapted to transmit wireless energy from an external energy transmitting device placed externally to a human body to an internal energy receiver placed internally in the human body, the apparatus comprising, a first electric circuit to supply electrical pulses to the external transmitting device, said electrical pulses having leading and trailing edges, said transmitting device adapted to supply wireless energy, wherein the electrical circuit being adapted to vary the lengths of first time intervals between successive leading and trailing edges of the electrical pulses and/or the lengths of second time intervals between successive trailing and leading edges of the electrical pulses, and wherein the transmitted wireless energy, generated from the electrical pulses having a varied power, the power depending on the lengths of the first and/or second time intervals.

The method and apparatus may be implemented according to different embodiments and features as follows:

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

When applying electrical pulses to the external energy source, the electrical pulses may generate an electromagnetic field over the external energy source, the electromagnetic field being varied by varying the first and second time intervals, and the electromagnetic field may induce electrical pulses in the internal energy receiver, the induced pulses carrying energy transmitted to the internal energy receiver. The wireless energy is then transmitted in a substantially purely inductive way from the external energy source to the internal energy receiver.

The electrical pulses may be released from the first electrical circuit with such a frequency and/or time period between leading edges of the consecutive pulses, so that when the lengths of the first and/or second time intervals are varied, the resulting transmitted energy are varied. When applying the electrical pulses, the electrical pulses may have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

BRIEF DESCRIPTION OF THE DRAWINGS

The present invention will now be described in more detail and with reference to the accompanying drawings, in which.

DETAILED DESCRIPTION OF PREFERRED EMBODIMENTS

Briefly described, wireless energy is transmitted from an external energy source located outside a patient and is received by an internal energy receiver located inside the patient. The internal energy receiver is connected to an electrically operable medical device implanted in the patient, for directly or indirectly supplying received energy to the medical device. An energy balance is determined between the energy sent by the external energy source and the energy received by the internal energy receiver, and the transmission of wireless energy is then controlled based on the determined energy balance. The energy balance thus provides an accurate indication of the correct amount of energy needed, which is sufficient to operate the medical device properly, but without causing undue temperature rise.

Figure 1:
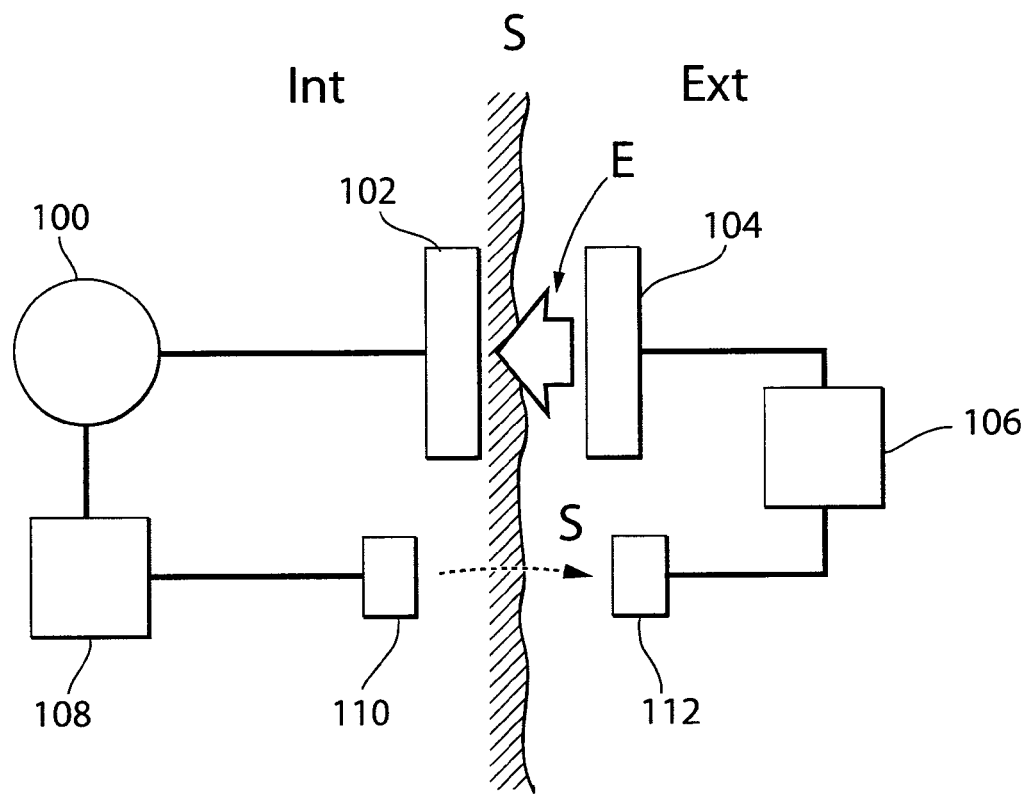
FIG. 1 is a schematic block diagram illustrating an arrangement for supplying an accurate amount of energy to an electrically operable medical device.

In FIG. 1, an arrangement is schematically illustrated for supplying an accurate amount of energy to an electrically operable medical device 100 implanted in a patient, whose skin is indicated by a vertical line S separating the interior "Int" of the patient from the exterior "Ext". The medical device 100 is connected to an internal energy receiver 102, likewise located inside the patient, preferably just beneath the skin S. Generally speaking, the energy receiver 102 may be placed in the abdomen, thorax, muscle fascia (e.g. in the abdominal wall), subcutaneously, or at any other suitable location. The energy receiver 102 is adapted to receive wireless energy E transmitted from an external energy source 104 located outside the skin S in the vicinity of the energy receiver 102.

As is well-known in the art, the wireless energy E may generally be transferred by means of any suitable TET-device, such as a device including a primary coil arranged in the energy source 104 and an adjacent secondary coil arranged in the energy receiver 102. When an electric current is fed through the primary coil, energy in the form of a voltage is induced in the secondary coil which can be used to operate a medical device, e.g. after storing the incoming energy in an energy storing device or accumulator, such as a battery or a capacitor. However, the present invention is generally not limited to any particular energy transfer technique, TET-devices or energy storing devices, and any kind of wireless energy may be used.

The amount of transferred energy can be regulated by means of an external control unit 106 controlling the energy source 104 based on the determined energy balance, as described above. Information representing the amount of energy received by the energy receiver 102 is sent from the energy receiver 102 to the external control unit 106 by means of the internal signal transmitter 110. Likewise, the energy source 104 sends information representing the amount of energy sent to the external control unit 106. In order to transfer the correct amount of energy, the energy balance and the required amount of energy can be determined by the external control unit by means of subtracting the amount of energy received from the amount of energy sent. Furthermore, an energy storing device or accumulator, not shown here, may also be connected to the energy receiver 102 for accumulating received energy for later use by the medical device 100. Alternatively or additionally, characteristics of such an energy storing device, also reflecting the required amount of energy, may be measured as well. The energy storing device may be a battery, and the measured characteristics may be related to the current state of the battery, such as voltage, temperature, etc. In order to provide sufficient voltage and current to the medical device 100, and also to avoid excessive heating, it is clearly understood that the battery should be charged optimally by receiving a correct amount of energy from the energy receiver 102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 106 is adapted to determine the energy balance and/or the currently required amount of energy, (either energy per time unit or accumulated energy) based on measurements made by the above-mentioned sensors. The internal control unit 108 is further connected to an internal signal transmitter 110, arranged to transmit a control signal S reflecting the received amount of energy, to an external signal receiver 112 connected to the external control unit 106. The external control unit 106 then calculates the energy balance by subtracting the amount of energy received from the amount of energy transmitted. The amount of energy transmitted from the energy source 104 may then be regulated in response to the received control signal.

Hence, the present solution employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by the medical device. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device.

The internal signal transmitter 110 and the external signal receiver 112 may be implemented as separate units using suitable signal transfer means, such as radio, IR (Infrared) or ultrasonic signals. Alternatively, the signal transmitter 110 and the signal receiver 112 may be integrated in the internal energy receiver 102 and the energy source 104, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 1 may operate basically in the following manner. The energy balance is first determined by the external control unit 106. The external control unit 106 then uses this information to control the energy source 104. Alternatively, the energy balance can be determined by the internal control unit 108 instead depending on the implementation. This process may be repeated intermittently at certain intervals during ongoing energy transfer, or may be executed on a more or less continuous basis during the energy transfer.

The amount of transferred energy can generally be regulated by adjusting various transmission parameters in the energy source 104, such as voltage, current, amplitude, wave frequency and pulse characteristics.

Figure 2:
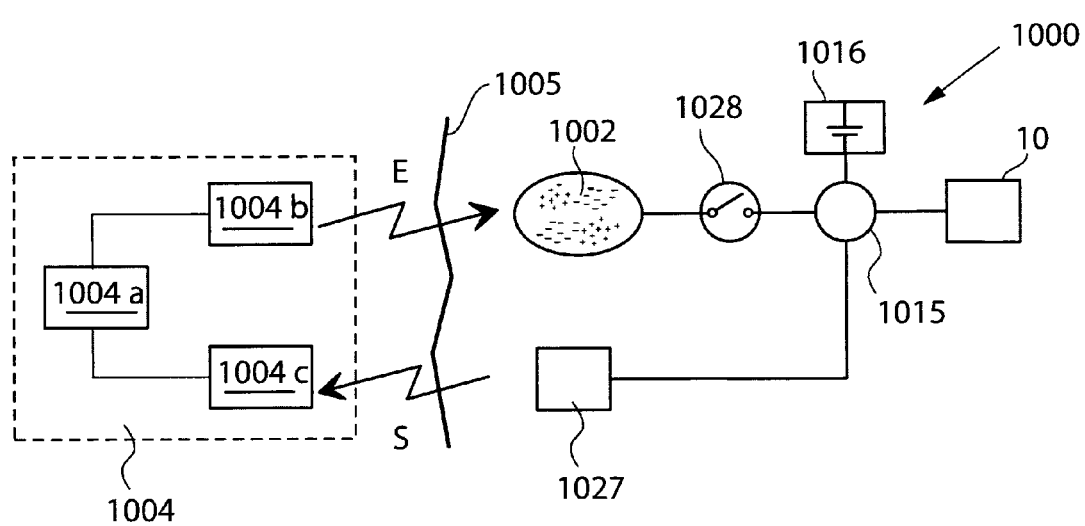
FIG. 2 is a more detailed block diagram of an apparatus for controlling transmission of wireless energy supplied to an electrically operable medical device implanted in a patient.

FIG. 2 Schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 17 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002. As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere. Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements.

Hence, the present solution according to the arrangement of FIG. 17 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004c may be implemented as separate units using suitable signal transfer means, such as radio, IR (Infrared) or ultrasonic signals. Alternatively, the internal signal transmitter 1027 and the external signal receiver 1004c may be integrated in the implanted energy-transforming device 1002 and the external energy source 1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 17 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement results from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 3:
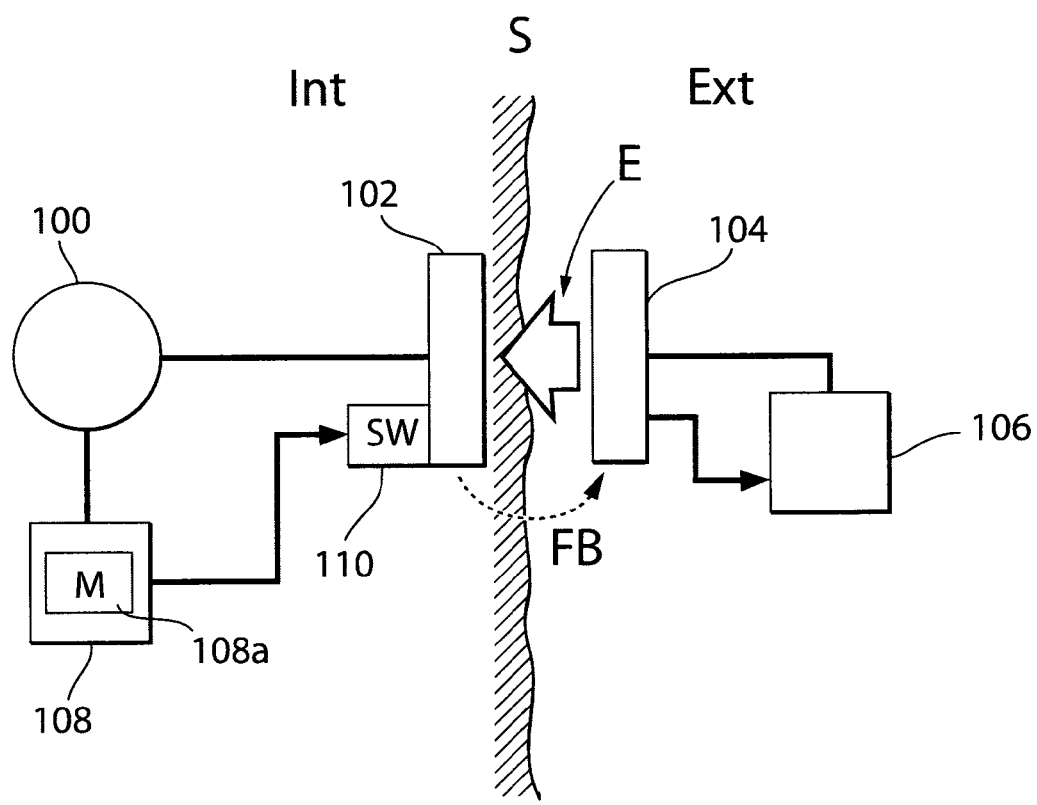
FIG. 3 is a schematic circuit diagram illustrating a proposed design of an apparatus for controlling transmission of wireless energy, according to a possible implementation example.

In FIG. 3, an arrangement is schematically illustrated for supplying an accurate amount of energy to an electrically operable medical device 100 implanted in a patient, whose skin is indicated by a vertical line S separating the interior "Int" of the patient from the exterior "Ext". The medical device 100 is connected to an internal energy receiver 102, likewise located inside the patient, preferably just beneath the skin S. Generally speaking, the energy receiver 102 may be placed in the abdomen, thorax, muscle fascia (e.g. in the abdominal wall), subcutaneously, or at any other suitable location. The energy receiver 102 is adapted to receive wireless energy E transmitted from an external energy source 104 located outside the skin S in the vicinity of the energy receiver 102.

The wireless energy E is transferred by means of a primary coil arranged in the energy source 104 and an adjacent secondary coil arranged in the energy receiver 102. When an electric current is fed through the primary coil, energy in the form of a voltage is induced in the secondary coil which can be used to operate the medical device 100, e.g. after storing the incoming energy in an energy storing device or accumulator, such as a battery or a capacitor, not shown in this figure.

The internal energy receiver 102 is adapted to transfer suitable feedback control information FB from the secondary coil to the primary coil by switching the secondary coil on and off to induce a detectable impedance load variation in the primary coil. This load variation is created and controlled to encode the feedback control information in a useful manner. The feedback control information thus communicated from the energy receiver 102 over to the energy source 104, generally relates to the energy for operating the medical device 100. The feedback control information is then used for controlling the transmission of wireless energy from the external energy source 104. The amount of transferred energy is regulated by means of an external control unit 106 controlling the energy source 104.

An internal control unit 108 may be implanted in the patient connected to the medical device 100. The internal control unit 108 is used to control the on and off switching of the secondary coil. The feedback control information FB may include at least one predetermined parameter relating to the received energy. The predetermined parameter may further be variable. When using the internal control unit 108, the feedback control information may relate to the received energy and may also require artificial intelligence to be generated.

The on and off switching of the secondary coil may be executed by means of an implantable switch 110 (SW) at the energy receiver 102, and the switch 110 is connected to and controlled by the internal control unit 108. The switch may be an electronic switch such as a transistor. Further, the internal control unit 108 may comprise a memory 108a for storing the transferred feedback control information FB.

The energy balance mentioned above may be determined by means of the external control unit 106 or the internal control unit 108, and the feedback control information will then relate to the determined energy balance. In that case, the external control unit 106 may be used to control the transmission of wireless energy E from the external energy source 104 based on the determined energy balance and using the received feedback control information FB.

The internal control unit 108 may be arranged to receive various measurements obtained by suitable sensors or the like, not shown, measuring certain characteristics of the medical device 100, somehow reflecting the energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by, e.g., body temperature, blood pressure, heartbeats and breathing.

Furthermore, an energy storing device or accumulator, not shown here, may also be connected to the energy receiver 102 for accumulating received energy for later use by the medical device 100. Alternatively or additionally, characteristics of such an energy storing device, also relating to the energy, may be measured as well. The energy storing device may be a battery, and the measured characteristics may be related to the current state of the battery, such as voltage, temperature, etc. In order to provide sufficient voltage and current to the medical device 100, and also to avoid excessive heating, it is clearly understood that the battery should be charged optimally by receiving a correct amount of energy from the energy receiver 102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Alternatively, sensor measurements can be transmitted to the external control unit 106 wherein the energy balance and/or the currently required amount of energy can be determined by the external control unit 106, thus basically integrating the above-described function of the internal control unit 108 in the external control unit 106. In that case, the internal control unit 108 can be omitted and the sensor measurements are comprised in the feedback control information FB. The energy balance and the currently required amount of energy can then be determined by the external control unit 106 based on those sensor measurements.

Hence, the present solution employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by the medical device. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device.

The feedback control information FB may further be modulated with respect to frequency, phase or amplitude.

To conclude, the energy supply arrangement illustrated in FIG. 1 may operate basically in the following manner, in the case when the transmission of wireless energy is controlled based on the energy balance described above. The energy balance may first be determined by the internal control unit 108. Feedback control information FB relating to the energy is also created by the internal control unit 108, and the feedback control information FB is transmitted from the energy receiver 102 to the energy source 104. Alternatively, the energy balance can be determined by the external control unit 106 instead depending on the implementation, as mentioned above. In that case, the feedback control information. FB may carry measurement results from various sensors. The amount of energy emitted from the energy source 104 can then be regulated by the external control unit 106, based on the determined energy balance, e.g. in response to the received feedback control information FB. This process may be repeated intermittently at certain intervals during ongoing energy transfer, or may be executed on a more or less continuous basis during the energy transfer.

The amount of transferred energy can generally be regulated by adjusting various transmission parameters in the energy source 104, such as voltage, current, amplitude, wave frequency and pulse characteristics.

What is claimed is:

1. A method for controlling transmission of wireless energy supplied to an electrically operable medical device implanted in a mammal patient, the method comprising the steps of:
    transmitting wireless energy from an external energy source by means of a primary coil located outside the patient, and
    receiving the transmitted wireless energy inductively in an internal energy receiver by means of a secondary coil located inside the patient, to directly or indirectly supply received energy to the medical device,
    receiving by an electronic circuit in the external energy source feedback information sent from inside the patient,
    comparing the feedback information with the amount of energy transmitted by the external energy source, wherein the feedback information is related to the amount of energy being received in the internal energy receiver,
    analysing by an analyzer in the electronic circuit the amount of energy being transmitted,
    using the received feedback information related to the amount of energy received in the internal energy receiver,
    determining a special energy balance by comparing the amount of transmitted energy and the feedback information related to the amount of received information, thus the feedback information is related to a coupling factor between the primary coil and the secondary coil,
    obtaining information about the coupling factor between the coils,
    calibrating the system for:
        a) finding an optimal place for the external coil in relation to the internal coil, and
        b) optimizing energy transfer, comparing the amount of energy transferred with the amount of energy received,
    detecting an energy balance after said calibration of the special energy balance being at least one of:
        a difference between the total amount of energy received by the internal energy receiver and the total amount of consumed and stored energy, being directly or indirectly measured over time, and
        an energy reception rate in the internal energy receiver corresponding to the total rate of energy consumption and storage of the apparatus,
    determining the energy balance based on at least one of:
        a detected change in the difference in the total amount of energy received by the internal energy receiver and the total amount of consumed and stored energy, and
        a detected change in the difference between the energy reception rate in the internal energy receiver and the total rate of energy consumption and storage,
    controlling the transmission of wireless energy from the external energy source, based on the determined energy balance to optimize energy transfer, during energy transfer.

2. The method according to claim 1, the method further comprising at least one of:
    consuming the energy after being stabilized in the at least one energy stabilizing unit of the medical device, and
    accumulating and stabilizing the energy received by the internal energy receiver in the at least one energy stabilizing unit, before the energy is supplied to the medical device.

3. The method according to claim 1, further comprising the step of stabilizing the energy received by the internal energy receiver by a capacitor, before the energy is supplied directly or indirectly to the medical device.

4. The method according to claim 1, further comprising the step of indicating by an indicator in the external energy source at least one of:
    a level of the coupling factor, and
    an optimal placement of said secondary coil in relation to said primary coil to optimize said coupling factor.

5. The method according to claim 1, further comprising the step of receiving the energy by the internal energy receiver being supplied to the medical device with at least one of:
    at least one constant voltage, wherein the constant voltage is created by a constant voltage circuitry, preferably the energy being supplied with at least two different voltages, including the at least one constant voltage, and at least one constant current, wherein the constant current is created by a constant current circuitry, preferably the energy being supplied with at least two different currents including the at least one constant current.

6. The method according to claim 1, further comprising the step of determining the energy balance based on a detected difference between the total amount of energy received by the internal energy receiver and the total amount of consumed and stored energy, the detected difference being related to the integral over time of at least one measured electrical parameter related to the energy balance.

7. The method according to claim 1, wherein the medical device comprises an energy storage device, comprising at least one of; a rechargeable battery, an accumulator and a capacitor.

8. The method according to claim 1, further comprising the steps of:
   accumulating and stabilizing the energy received by the internal energy receiver in at least one of:
      an energy stabilizing unit before the energy is supplied to the medical device, and
      an energy storage device, and
   supplying the energy to at least one of;
      the medical device, and
      the energy storage device,
   supplying with at least one constant voltage, at least one constant current or at least one constant current and at least one constant voltage, as maintained by a constant voltage circuitry, constant current circuitry or one constant voltage and constant current circuitry, when at least one of; the medical device and energy storage device is supplied with two different voltages or currents, at least one voltage or current is constant, maintained by the constant voltage or current circuitry.

9. The method according to claim 2, further comprising the step of determining the energy balance by detecting at least one of:
   a change in the current amount of accumulated energy in the energy stabilizing unit,
   the direction and rate of change in the current amount of accumulated energy in the energy stabilizing unit,
   a change in the current amount of accumulated energy in the energy stabilizing unit,
   the direction and rate of change in the current amount of accumulated energy in the energy stabilizing unit.

10. The method according to claim 8, further comprising the step of determining the energy balance by detecting at least one of:
   a change in the current amount of accumulated energy in the energy stabilizing unit,
   the direction and rate of change in the current amount of accumulated energy in the energy stabilizing unit,
   a change in the current amount of accumulated energy in the energy stabilizing unit,
   the direction and rate of change in the current amount of accumulated energy in the energy stabilizing unit.

11. The method according to claim 1, further comprising the step of using sensors for at least one of:
   measuring characteristics of the medical device,
   detecting the current condition of the patient, and
   reflecting the required amount of energy needed for proper operation of the medical device,
   determining at least one of:
      electrical parameters, physical parameters or electrical and physical parameters of the medical device, and
      physical parameters of the patient, and
   transmitting the energy with a transmission rate which is determined based on the parameters.

12. The method according to claim 9, comprising sensors for at least one of:
   measuring characteristics of the medical device,
   detecting the current condition of the patient, and
   reflecting the required amount of energy needed for proper operation of the medical device,
   determining at least one of:
      electrical parameters, physical parameters or electrical and physical parameters of the medical device, and
      physical parameters of the patient, and
   transmitting the energy with a transmission rate which is determined based on the parameters.

13. The method according to claim 7, wherein the energy storage device of the medical device comprises a first storage device and a second storage device, and wherein the method further comprises the steps of:
   storing the energy received by the internal energy receiver first in the first storage device, and then supplying the energy from the first storage device to the second storage device at a later stage,
   determining the energy balance by detecting at least one of:
      the current amount of energy stored in the first storage device, wherein the transmission of wireless energy being controlled such that a storing rate in the second storage device corresponds to an energy reception rate in the internal energy receiver,
      the total amount of stored energy in the first storage device,
      a change in the current amount of stored energy in the first storage device, or
      a direction and rate of change in the current amount of stored energy in the first storage device.

14. The method according to claim 13, further comprising the step of using a constant current circuitry for supplying stabilized energy from the first storage device to the second storage device with a constant current until a measured voltage over the second storage device reaches a predetermined maximum voltage, and thereafter supplied from the first storage device to the second storage energy storage device with a constant voltage, as maintained by a constant voltage circuitry, so the transmission of wireless energy can be turned off when a predetermined minimum rate of transmitted energy has been reached.

15. The method according to claim 1, comprising the step of using an internal control unit and an implantable switch for executing an on and off switching of the secondary coil as being controlled by the internal control unit.

16. The method according to claim 13, wherein the first storage device is involved in at least one of the following steps:
   being charged at a relatively higher energy charging rate as compared to the second storage device, thereby enabling a relatively faster charging, and
   being charged at multiple individual charging occasions more frequently as compared to the second storage device, thereby providing relatively greater life-time in terms of charging occasions.

17. The method according to claim 1, further comprising the step of detecting a change in said difference, the change in the amount of consumed energy is detected by determining over time the derivative of a measured electrical parameter related to the amount of consumed energy, the derivative corresponding to the rate of the change in the amount of consumed energy, wherein the rate of change includes the direction and speed of the change, wherein a rate of change of the electrical parameter is detected, the derivative being related to the detected change rate.

18. The method according to claim 9, further comprising the step of detecting a change in said difference, the change in the amount of consumed energy is detected by determining over time the derivative of a measured electrical parameter related to the amount of consumed energy, the derivative corresponding to the rate of the change in the amount of consumed energy, wherein the rate of change includes the direction and speed of the change, wherein a rate of change of the electrical parameter is detected, the derivative being related to the detected change rate.

19. The method according to claim 6, further comprising the step of detecting the difference related to the integral over time of at least one measured electrical parameter related to said energy balance, the integral may be determined for a monitored voltage, current or voltage and current related to the energy balance.

20. The method according to claim 11, further comprising the steps of:
   determining at least one of:
      electrical, parameters, physical parameters or electrical and physical parameters of the medical device, and
      physical parameters of the patient, and
   transmitting the wireless energy for at least one of: consumption and storage, according to a transmission rate per time unit which is determined based on said parameters.

21. The method according to claim 11, further comprising the step of:
   determining for energy storage at least one of;
      electrical parameters, physical parameters or electrical and physical parameters of the medical device, and
   physical parameters of the patient, and
   turning off the transmission of wireless energy automatically when a total amount of energy has been stored, controlling the transmission of wireless energy such that an energy reception rate at the internal energy receiver corresponds to the storing rate.

\* \* \* \* \*